United States Patent [19]

Fukukita et al.

[11] Patent Number: 4,641,260

[45] Date of Patent: Feb. 3, 1987

[54] DIGITAL SIGNAL PROCESSING APPARATUS FOR A BLOOD FLOWMETER USING ULTRASOUND DOPPLER EFFECT

[75] Inventors: Hiroshi Fukukita, Tokyo; Ryobun Tachita, Kawasaki; Kuniaki Fukaya, Atsugi; Tsutomu Yano, Kawasaki, all of Japan

[73] Assignee: Matsushita Electric Industrial Co., Ltd., Japan

[21] Appl. No.: 558,274

[22] Filed: Dec. 5, 1983

[30] Foreign Application Priority Data

Dec. 3, 1982 [JP] Japan ............................. 57-212934

[51] Int. Cl.[4] ...................... G06F 11/00; G06F 15/35; G06F 15/42; G06F 7/34
[52] U.S. Cl. .................................. 364/737; 364/726; 364/416
[58] Field of Search ...................... 364/726, 416, 737; 343/5 FT; 382/43

[56] References Cited

U.S. PATENT DOCUMENTS

| | | | |
|---|---|---|---|
| 3,673,399 | 6/1972 | Hancke et al. | 364/726 |
| 4,225,864 | 9/1980 | Lillington | 343/5 FT |
| 4,257,278 | 3/1981 | Papadofrangakis et al. | 364/416 |
| 4,265,126 | 5/1981 | Papadofrangakis et al. | 364/416 |
| 4,393,457 | 7/1983 | New | 364/726 |

OTHER PUBLICATIONS

Godbole et al, "Realtime Spectrum Analysis Using a Microprocessor Peripheral"; Conference ICASSP 81, IEEE International Conf. on Acoustics Speech and Signal Processing, pp. 654–657, Mar. 30–Apr. 1, 1981.
Chwastyk; "A Fast Digital Spectral Analyzer"; IEEE Trans. on Instrumentation and Measurement; vol. IM-20, No. 4, pp. 198–201, Nov. 1971.

Primary Examiner—James D. Thomas
Assistant Examiner—Dale M. Shaw
Attorney, Agent, or Firm—Lowe, Price, Leblanc Becker & Shur

[57] ABSTRACT

A digital signal processing apparatus is shown which is applicable for real time operation in the power spectrum of the detected outputs of ultrasonic Doppler blood flowmeter. The apparatus comprises a digital operating means, a memory means which is connected to said digital operating means to transfer data thereto and receive data therefrom, a fixed instruction generating portion for generating operating code for the digital operating means and addresses for the memory means, a read only memory for storing data of a squaring operation which has address inputs at the bit position selected as most suitable from the input data bus line of said digital operating means, an overflow detecting means when input data exceeds the region of the address input, and digital saturation circuit, whereby the power spectrum can be calculated by fundamental algorithm of WFTA having a smaller number of operating steps than algorithm FFT.

6 Claims, 4 Drawing Figures

DIGITAL SIGNAL PROCESSING APPARATUS FOR A BLOOD FLOWMETER USING ULTRASOUND DOPPLER EFFECT

BACKGROUND OF THE INVENTION

The present invention relates to a digital signal processing apparatus for use in analyzing power spectrum of discrete data sequences such as detected outputs of a blood flowmeter using ultrasound Doppler effect (hereinafter called "Doppler blood flowmeter").

Recently, the Doppler blood flowmeter has been put in practical use in circulatory system diagnostic field. The Doppler blood flowmeter is capable of measuring blood flow speed in a human blood vessel by frequency analyzing an echo signal which is reflected from blood corpuscles and shifted in frequency by the Doppler effect. In the Doppler blood flowmeter, an ultrasonic pulse train having constant period is transmitted in a human body from an ultrasonic probe. The ultrasonic pulse is reflected by the blood corpuscles in a blood and shifted in frequency by Doppler modulation. The Doppler shifted echo signal is received by the ultrasonic diagnostic probe and amplified by an amplifier. The amplified echo signal is multiplied in a detector by signals each of which is formed from a reference pulse train by shifting 0° and 90° in phase. Each of the multiplied signals is integrated by an integrating circuit in a determined gating period and added to an analog-to-digital converter after removing low frequency signals corresponding to blood vessel wall, valve and so on through a high-pass filter. A digital signal obtained from the analog-to-digital converter is frequency analyzed by a digital Fourier transformer and displayed as a sonogram.

In the digital Fourier transformer, an exclusive digital signal processing unit having a fundamental algorithm of FFT (Fast Fourier Transform) is usually employed. For example, a Doppler blood flowmeter system using FFT algorithm is known in which the power spectrum of complex data sequences of 128 points is analyzed at intervals of two (2) milliseconds. In the FFT algorithm each of real addition and subtraction and real multiplication of a fixed multiplier involve 2,368 steps and 1,152 steps, respectively. To perform the above noted steps of FFT operation within a one (1) millisecond interval, a high speed digital multiplier is required. An IC (integrated circuit) having a 100 nanoseconds operation time is now available, but the IC cannot select bit length freely to obtain sufficient precision of operation. Furthermore, the IC is not of a standard type and very costly.

On the other hand, it is desirable to simplify the operating circuit by adopting an operating circuit using fixed decimal point rather than an operating circuit using floating decimal point. Accordingly, the operating circuit using fixed decimal point is used in the conventional system. However, overflow in the operation sometimes occurs in the operating circuit using fixed decimal point because the echo signals from the blood vessel wall or valve moving in high speed are mixed with the echo signal from the corpuscles. The echo signals from the blood vessel wall or valve moving in high speed have large power spectra and lie within the range of the echo signal from the blood corpuscles. Therefore, the echo signals from the blood vessel wall or valve is impossible to remove by a filter circuit.

SUMMARY OF THE INVENTION

According to the invention, a digital signal processing apparatus of a simplified construction is obtained which allows operation in the power spectrum of the detected outputs of the Doppler blood flowmeter at a considerably high speed with a high degree of precision.

The digital signal processing apparatus of the invention comprises a digital operating means, a command signal generating means which generates coded signals for driving the digital operating means and address signals for a memory means connected to the digital operating means, a read only memory means containing data for operating squaring, an overflow detecting means for detecting data which are out of the range of input address signal to the read only memory, and a digital circuit for obtaining a saturated value when the overflow occurs, whereby the power spectrum of the detected outputs of the Doppler blood flowmeter can be operated on the algorithm WFTA (Winograd Fourier Transform Algorithm) having a smaller number of operating steps than FFT in a simple circuit.

BRIEF DESCRIPTION OF THE DRAWINGS

The invention will be further described with reference to the accompanying drawings, in which.

DETAILED DESCRIPTION

Figure 1:
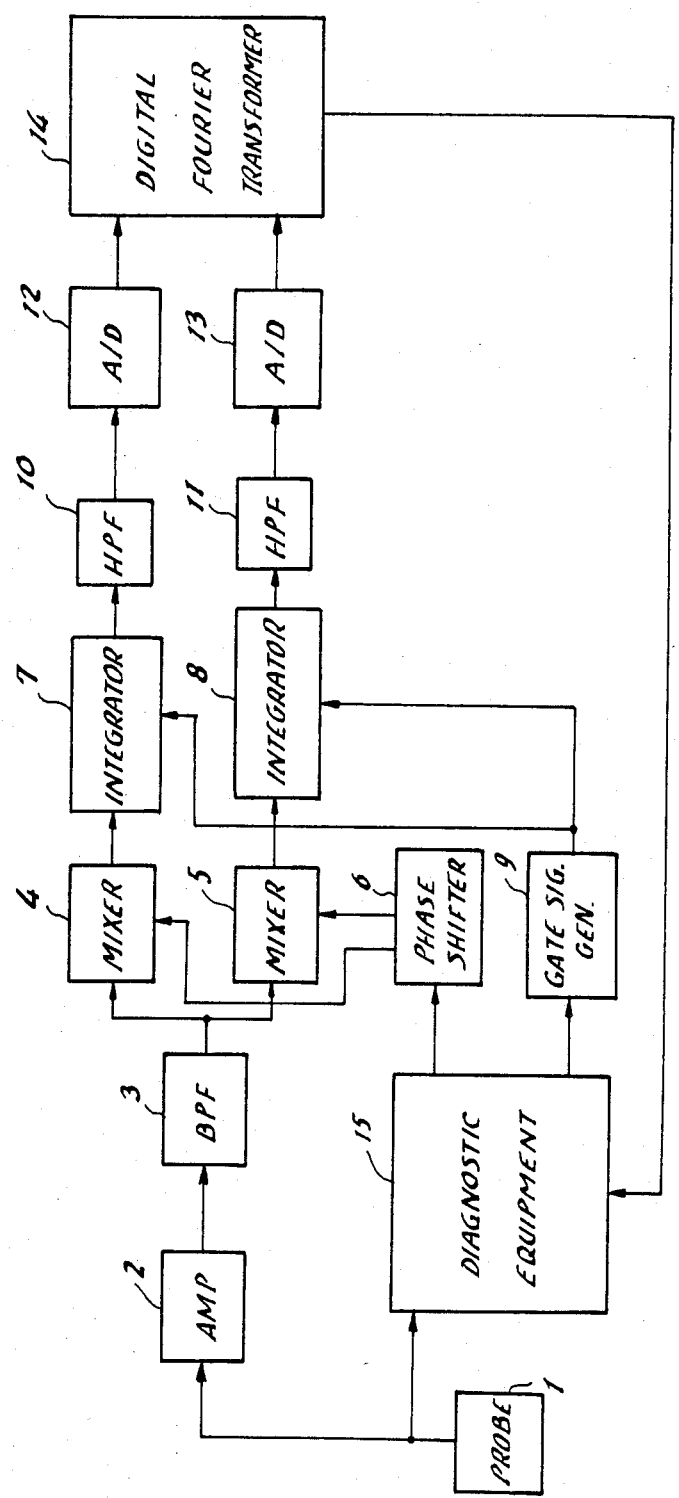
FIG. 1 is a block diagram of an embodiment of the Doppler blood flowmeter having the digital signal processing apparatus of the invention.

Referring now to FIG. 1, a pulse train of constant period is emitted into a human body from an ultrasonic diagnostic probe 1. The pulse signal is reflected from blood corpuscles in a blood vessel and Doppler modulated by blood flow. The modulated signal is received by the ultrasonic diagnostic probe 1 and amplified by an amplifier 2. The output of the amplifier 2 is supplied to a base-pass filter (BPF) 3 to remove noise components and is supplied to mixers 4, 5. The mixers 4, 5 multiply the output of the BPF 3 and signals from a phase shifter 6, the signals from the phase shifter being a reference pulse signal having a phase difference of 90° with respect to each other. Each of the multiplied outputs of the mixers 4, 5 is integrated by integrators 7, 8 in a period determined by gate signals from a gate signal generating circuit 9 and converted into a digital signal by analog-to-digital converters 12, 13 after removing low frequency components such as echo signals from blood vessel wall by high-pass filters (HPF) 10, 11. The digital signals from the analog-to-digital converters are frequency analyzed by a digital Fourier transformer 14 and applied to a diagnostic equipment 15 to display the spectrum distribution of the output from the digital Fourier transformer in the form of a sonogram.

Figure 2:
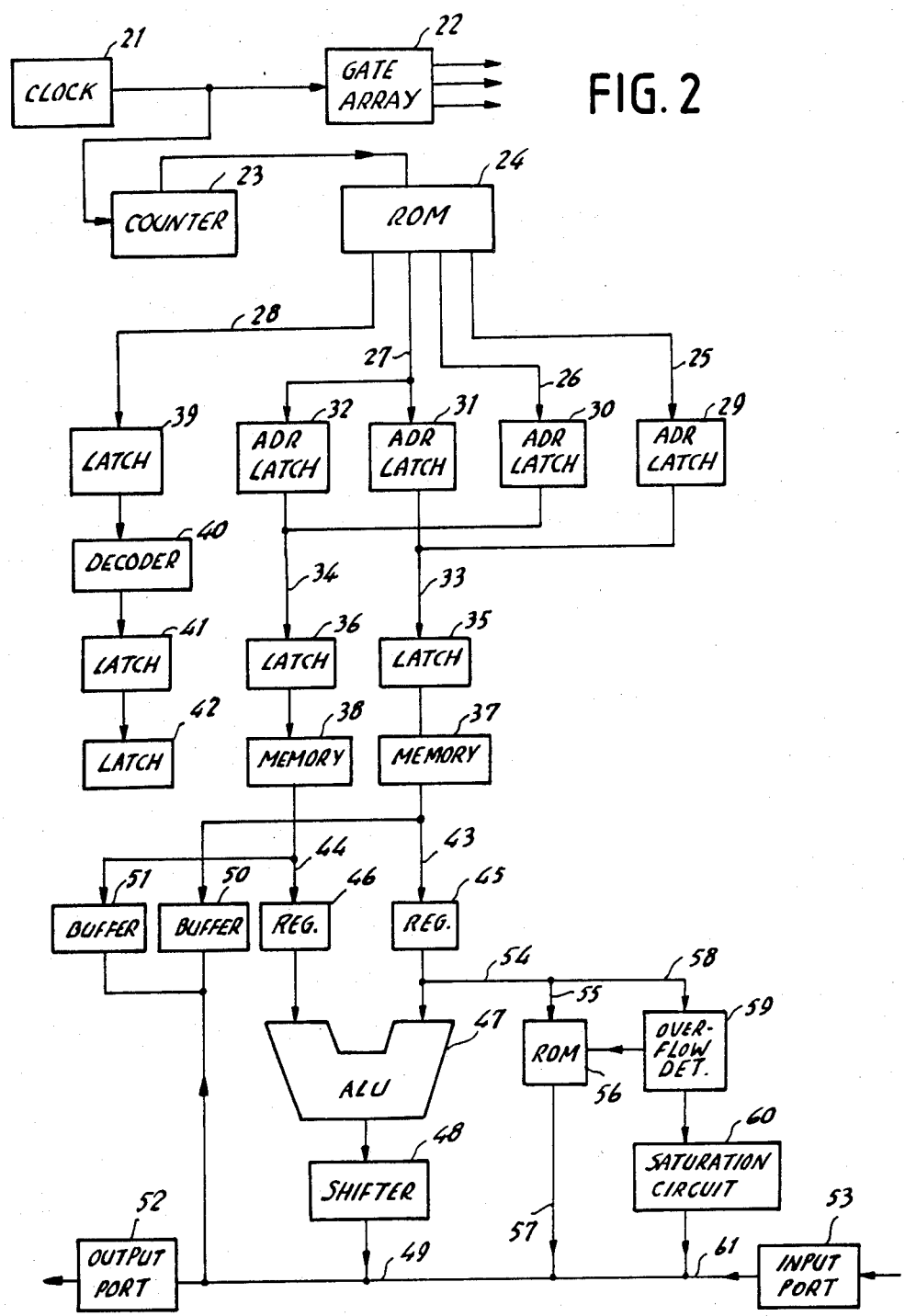
FIG. 2 is a block diagram of an embodiment of the digital signal processing apparatus of the invention.

FIG. 2 is a block diagram of the digital Fourier transformer 14 of FIG. 1. A clock pulse from a clock pulse generator 21 is supplied to a gate array 22 for generating timing pulses to drive each of the blocks mentioned hereinafter. The clock pulse is also supplied to a counter 23 which controls address inputs of a read only memory 24 (hereinafter called ROM) of a fixed command signal generating portion. The ROM 24 outputs memory read address signals, memory write address signals and operating code signals. Each of address latches 29 and 30 latches the memory read address signals for memories 37 and 38 via bus lines 25 and 26 respectively. Each of address latches 31 and 32 latches the memory write address signals for memories 37 and 38 via bus line 27. The operating code signals is latched in a latch 39 via bus 28. The outputs from the address latches 29 and 31 are supplied to a latch 35 by multiplying on a bus line 33 and the output thereof controls an address of A memory 37. Similarly, the outputs from the address latches 30 and 32 are multiplied on the bus line 34 and stored in a latch 36, the output thereof controlling an address of B memory 38. The operating code signals are supplied to a latch 39 via a bus line 28 to control an operating code decoder 40. The outputs of the decoder 40 are delayed a predetermined time by latches 41 and 42 and supplied to each block. Each of the outputs from the A memory 37 and B memory 38 is supplied to registers 45 and 46 connected to digital operating portion composed of an arithmetic logic unit 47 (hereinafter called "ALU") and a shifter 48. The output of the shifter 48 is supplied to an output port 52 via output bus line 49.

An input port 53 receives a digital signal from the analog-to-digital converter shown in FIG. 1 and written into the A memory 37 and B memory 38 through buffers 50 and 51. The output of the input port is controlled by the operating codes from the latch 41 and 42. While, the input address of each of the A memory 37 and B memory 38 is designated by the WRITE address from the address latches 35, 36.

The written data in the A memory 37 and B memory 38 are read out by the READ address from the address latch 35 and 36 and supplied to the ALU. In the ALU 47 and the shifter 48, arithmetic operation of addition, subtraction or shift operation and so on are performed in accordance with said operating codes. The results of arithmetic operation are written into the A memory 37 and B memory 38 in response to WRITE address from the address latches 35 and 36 via the buffers 50 and 51. Otherwise, the arithmetic results are supplied to the diagnostic equipment shown in FIG. 1 through the output portion 52.

One example of DFT (Discrete Fourier Transform) operation dealing with complex data of 120 points will now be described. In the DFT operation, WFTA algorithm is adopted. WFTA is known in "IEEE trans. ASSP-25, No. 2, p.152, 1977". In the WFTA algorithm, a number of operating steps for complex data of 120 points is 2,076 steps in real multiplication of fixed multiplier. The real multiplication of n bit fixed multiplier can be performed by addition, substraction and shift operation of mean value n/5 steps using the ALU and an n bit shifter by means of canonical coding of the multiplier.

The real multiplication of fixed multiplier of WFTA's 288 steps for complex data of 120 points having a wordlength of 16 bits is performed by approximately 1,600 steps of addition, subtraction and shift operation using ALU 47 and a 4-bit shifter. If use is made of a 16-bit shifter, a number of steps can be further reduced. According to the above condition, WFTA for the complex data of 120 points is converted into approximately 3,700 steps (1,600 steps and 2,076 steps) of addition, subtraction, and shift operation. To perform these steps of operation within one (1) millisecond interval, it is necessary to reduce the operating time of each step to less than about 250 nanoseconds. In FIG. 2, data flow in one operating step involves (1) reading data from A memory 37 and B memory 38, (2) latching data in registers 45 and 46, (3) transmitting output signals from ALU 47 to buffers 50 and 51 through shifter 48, and (4) writing data into A memory and B memory. By using a standard digital IC it is possible to reduce the data flow time to less than 250 nanoseconds. Similarly, the time required for the data output cycle of the ROM 24 can be reduced to less than 250 nanoseconds by using a standard ROM having an access time of 200 nanoseconds. As a result, the circuit assembly shown in FIG. 2 is capable of operating WFTA of complex data of 120 points within the period of one millisecond.

The circuit assembly shown in FIG. 2 makes it possible to process the detected outputs of the Doppler blood flowmeter within one (1) millisecond without costly multiplication IC. The high speed processing time of one (1) millisecond allows high resolution for sonogram patterns for accurate diagnostic purposes. Furthermore, the digital operating portion composed of ALU 47 and shifter 48 can lend itself to adaptation to changes in data wordlength compared with conventional digital multipliers.

Now, the arithmetic operation for power spectrum will be explained. The power spectrum is calculated by a formula:

$$P = X^2 + Y^2 \qquad (1)$$

where P is the power spectrum, X is a real part of the Fourier spectrum, and Y is a complex part of the Fourier spectrum. In FIG. 2, ROM 56, overflow detector 59 and digital saturation circuit 60 consist the operating portion of the power spectrum. Bus line 54, which is one of the n bit input data bus line of the ALU 47, is connected to the ROM 56 by ROM address bus line 55 at the bit position m to m+l−1 (where m and l are integers, and bit position 0=SLB). The ROM 56 has l bit input and k (k is an integer) bit output and stores square-operated data to obtain output data which correspond to square of input data. The bit position m+l−1 to n−1 (where n is an integer) of the input bus line 54 of the ALU 47 forms an overflow bus line 58 and is connected to the input of the overflow detector 59. The overflow detector 59 is connected to the digital saturation circuit 60. The output bus line 61 of j (j is an integer) bit is connected to the output bus line 49 of the shifter 48 at the bit position n−j to n−1.

Table 1 shows operating states of bus line 54, 55, 57 and 61 when performing squaring.

TABLE 1

| Data on Bus Line 54 | | Input of ROM 56 | Output of ROM 56 | Output of Digital Saturation Circuit 60 |
| MSB | LSB | | | |
| --- | --- | --- | --- | --- |
| 01111 | 11111111111 | Positive OVF | High Impedance | 01111111, ACTIVE |
| 00000 | 10000000000 | " | " | " |
| 00000 | 01111111111 | Positive Upper Limit | ACTIVE | High Impedance |
| 00000 | 00000000000 | 0 | " | " |
| 11111 | 11111111111 | −1 | " | " |

TABLE 1-continued

| Data on Bus Line 54 | | Input of ROM 56 | Output of ROM 56 | Output of Digital Saturation Circuit 60 |
| --- | --- | --- | --- | --- |
| MSB | LSB | | | |
| 11111 | 10000000000 | Negative Lower Limit | " | " |
| 11111 | 01111111111 | Negative OVF | High Impedance | 01111111, ACTIVE |
| 10000 | 00000000000 | " | " | " |
| Detector 59 INPUT | ROM 56 INPUT | | | |

During this operation, the outputs of shifter 48 and input portion 53 have a high impedance. In Table 1, l=11, m=0, k=16 and j=8 and fixed decimal point data is expressed by a complement of "2". As shown in Table 1, when the data on bus line 54 exceeds the input limits of the ROM 56, the output impedance of ROM 56 goes high, and the output impedance of the digital saturation circuit 40 goes low, or ACTIVE to supply "01111111" to upper side j(=8) bit of the output bus line 49. In this line, a lower significant 8 bit of the output bus line 49 is in floating state and the data is uncertain. However, the upper side 8 bit expresses a very large positive number which substantially digitally saturates the results of the square operation. In this example, the ROM 56 has an 11-bit address input and a 16-bit output. This type of ROM can be constructed of two ROM chips of 16K (=2,048×8 bit), because $2^{11}$=2,048. This construction is less costly than high-speed digital multiplication ICs.

Figure 3:
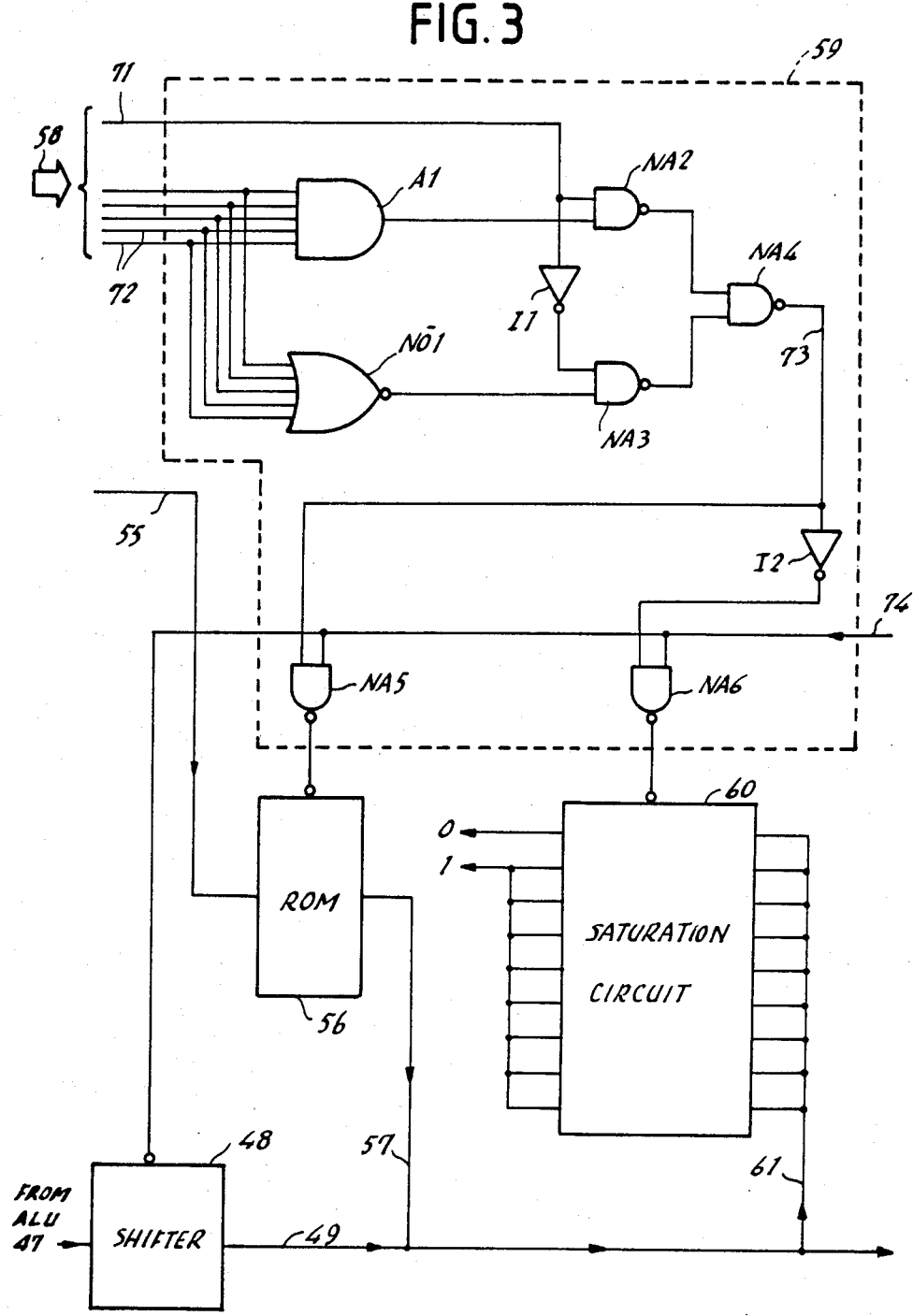
FIG. 3 is a detailed block diagram of a portion of FIG. 1.

FIG. 3 is a detailed block diagram showing the operating portion of the power spectrum shown in FIG. 2 which is constructed by standard digital ICs. A region 59 surrounded by dotted line corresponds to the overflow detector 59 of FIG. 2. A signal line 71 corresponds to bit position 15 (MSB, code bit) of bus line 54 of ALU 47 in FIG. 2 and a signal line 72 corresponds to bit position 14 to 10 of the same. The signal lines 71 and 72 constitute the overflow bus line 58. A1 shows an AND gate circuit having five (5) input lines, NO1 shows a NOR gate circuit having five (5) input lines, NA2 to NA 6 show NAND gate circuits having two (2) input lines, and I$_1$, I$_2$ show inverter circuits. As shown in Table 1, when overflow occurs, all the data of the overflow bus line 71 and 72 are "0" or "1". In this case, the output of the NAND gate circuit NA4 is "0". When a squaring operation is performed, a control line 54 which is one of micro operating codes explained in FIG. 2, becomes "1", whereby the output impedance of the shifter 48 goes high and the output of the NAND gate circuit NA6 becomes "0". When the output of the NAND gate circuit NA 6 becomes "0", a buffer 60 having eight (8) inputs which constitute the digital saturation circuit 60 shown in FIG. 2 becomes ACTIVE to supply input data "01111111" to output bus line 49. The time required for said process is the time required for data transmission of five (5) stage gate circuits and data process in the buffer 60, and this length time can be made less than 40 nanoseconds by using a standard digital IC. The output of the NAND gate NA 5 is now "1", and the ROM 56 is not driven.

When no overflow occurs, the output of the NAND gate NA4 becomes "1". In this case, the ROM 56 is driven while the digital saturation circuit is not. The ROM 56 corresponds to the ROM 56 in FIG. 2 which performs the squaring operation. This ROM 56 is realized by a standard bipolar ROM having an access time of near 50 nanoseconds. The input address bus line 55 of the ROM 56 connects to bit position 10 to 0 of the ROM's input.

With the arrangement just described, the time required for one squaring operation involving reading data from and writing it into the A memory 37 is reduced to less than 250 nanoseconds which is comparable to the time taken by addition, subtraction and shift operation.

When the input from the control line 74 is "0", the output of the shifter 28 becomes ACTIVE and addition, subtraction and shift operation explained hereinbefore are performed and the ROM 56 and the buffer 60 are not driven.

In FIG. 2 it is possible to arrange the shifter 48 between register 46 and ALU 47. In this case, the outputs from ROM 56 and digital saturation circuit 60 are supplied to the output bus line of the ALU 47.

According to the embodiment described above, the detected output of the Doppler blood flowmeter can be analyzed at a considerably high speed with the use of a very simplified inexpensive circuit. When the output exceeds a predetermined level, the output is treated as a noise signal and not supplied to the ROM for squaring operation but is supplied to the overflow detector automatically.

Figure 4:
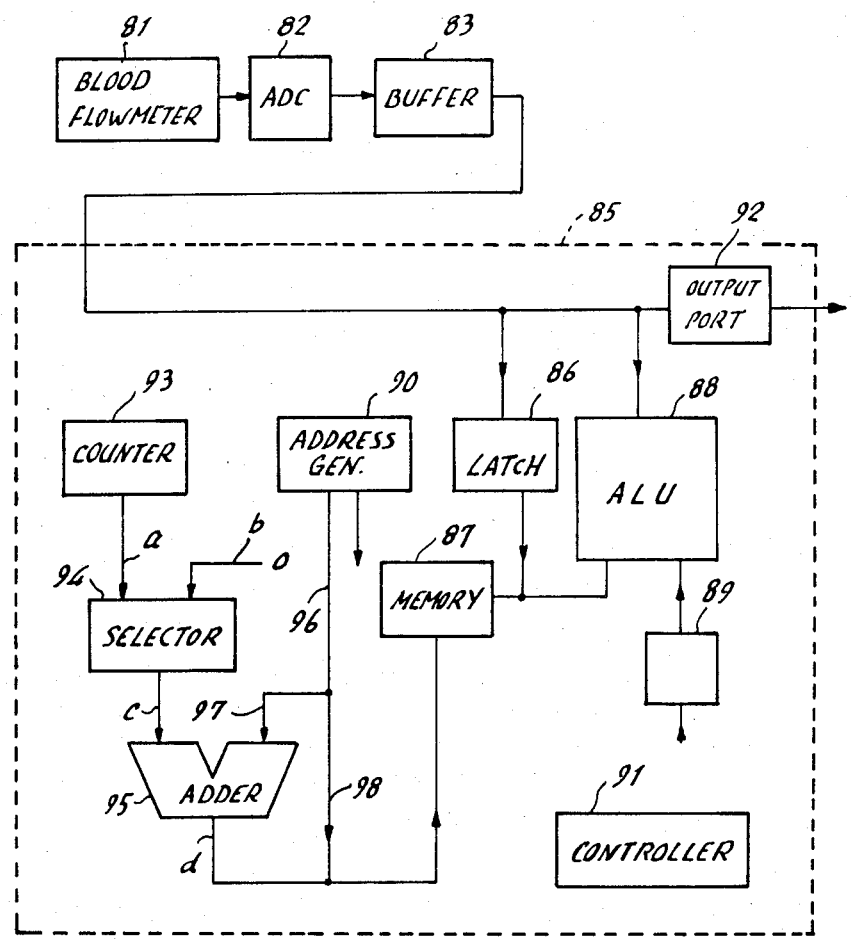
FIG. 4 is a block diagram of another embodiment of the digital signal processing apparatus of the invention.

Referring now to FIG. 4, another embodiment of the invention will be explained.

FIG. 4 shows a portion of digital data to be transferred from the Doppler blood flowmeter to memories. A numeral 81 designates the Doppler blood flowmeter which outputs analog data to be analyzed. The analog data is converted into digital data by an analog-to-digital converter 82 and supplied to an interface buffer 83. The interface buffer 83 corresponds to the input portion of FIG. 2. A portion surrounded by dotted lines 85 is a DFT digital signal processing apparatus. In this embodiment, the operating algorithm is WFTA which processes on complex data of 120 points within 1.6 milliseconds. Therefore, 8(=$2^7$−120) complex data is renewed in every operating process cycle. A memory 87 (which corresponds to the A memory 37 and B memory 38 in FIG. 2) is divided into plural regions for receiving input data and performing DFT operation, and it is possible to receive input data from the interface buffer 83 during DFT operation. Therefore, input data transfer speed can be made slow to such a degree that it nearly equals the sampling speed of the Doppler blood flowmeter. The memory 87 has addresses 0 to 1,023 which are realized by a standard static IC RAM. The input data receiving region of the memory 87 is assigned addresses 0 to 255 for complex input data of 120 points. A numeral 86 designates a latch which corresponds to the buffers 50 and 51 in FIG. 2. A numeral 88 shows the ALU to which a multiplier for WFTA operation is supplied from a ROM 89. An address generator 90, which corresponds to the ROM 24, latches 29 to 32, 35, 36 and 39 in FIG. 2, generates address signals for the memory 87 and the ROM 89. A controller 91 corresponds to the clock pulse generator 21 and gate array 22 in FIG. 2, and controls drive timing of each part of the DFT processing apparatus and requests input data to be applied to the interface buffer 83. The interface buffer 83 transfers the data to the latch 86 when it receives a data request from the controller 91 and awaits the next data request. The address generator 90 and controller 91 constitute a fixed instruction generating portion. A numeral 92 is a fast-in fast-out register for extracting the operated results which form the output port 52 in FIG. 2.

A 4-bit counter 93 is provided for counting operating passes in synchronism with operation process cycles. The output signal a of the counter 93 is supplied to a selector 94. The selector 94 selects 4-bit data output a when the address generator 90 generates an address corresponding to the input data buffer region, and selects 0 data output b except in the case mentioned above under the instruction of the controller 91. In a 4-bit address adder 95, a 4-bit output c from the selector 94 and the output of the address generator 90 which is supplied via an address bus line 97 corresponding to bit positions 4 to 7 of an address bus line 96 of the address generator are added. In this case the most significant bit of the counter 93 and bit position 7 of the address bus 97 are coincident with each other. The address bus line 96 is of a 10-bit line to carry the address of 1025 words of the memory 87. Bit positions 0 to 3 and 8 to 9 thereof consist address bus line 98 connected to the address input of the memory 87. The address adder 95 supplies 4-bit output d to the address input of the memory 87 at the bit positions 4 to 7.

When the address generator 90 generates addresses 0 to 255 corresponding to the input data buffer region of the memory 87 the address input of the memory 87 is updated by the address adder 95 in every operating cycle. Table 2 shows the state of the updating operation. In Table 2, the notations are as follows:

NCYCLE: cycle number of operation process;
NPASS: output of the counter 93;
NR: address input of the memory 87 corresponding to read address outputs 0 to 239 of the address generator 90;
NW: address input of memory 87 corresponding to write address outputs 240 to 255 of the address generator 90.

TABLE 2

| NCYCLE = 0 | NPASS = 0 |
| NR = 0~239 | NW = 240~255 |
| NCYCLE = 1 | NPASS = 1 |
| NR = 16~255 | NW = 0~15 |
| NCYCLE = 2 | NPASS = 2 |
| NR = 32~255, 0~15 | NW = 16~31 |
| . | . |
| . | . |
| . | . |
| NCYCLE = 15 | NPASS = 15 |
| NR = 240~255, 0~223 | NW = 224~239 |
| NCYCLE = 16 | NPASS = 0 |
| NR = 0~239 | NW = 240~255 |
| NCYCLE = 17 | NPASS = 1 |
| NR = 16~255 | NW = 0~15 |

Eight (8) complex data written into address 240 to 255 of the address generator 90 in operating cycle NCYCLE=0 are read out in NCYCLE=1 and new 8 complex data are written into addresses 0 to 15 of the address generator 90. When NCYCLE=16, NPASS becomes 0 and address number returns to that of the state NCYCLE=0.

As shown above, when 8 data in 120 complex data are renewed in every operation process cycle, 4-bit address adder 95 is connected to the bit position of 4 to 7 of the address bus 97 and adds the output of the counter for operating passes, thereto. The 4-bit counter 93, data selector 94 and adder 95 are standard ICs available on the market.

In the embodiment described above, an input data buffer region is assigned to the high speed memory 87 in the DFT processing apparatus to transfer the data from the Doppler blood flowmeter at a low speed. The speed of data transfer is on the same order as that of the sampling speed of the Doppler blood flowmeter. Therefore, the interface buffer 83 takes in the low speed data from the Doppler blood flowmeter and responds to the request for low speed data transfer flom the DFT processing apparatus. As a result, low speed data from the Doppler blood flowmeter can transfer directly to the high speed memory for operation by omitting means for converting data transfer speed such as fast-in fast-out register at data input portion.

What is claimed is:

1. A digital signal processing apparatus comprising a digital processing means,
n-bit input and output data bus lines for said digital processing means,
a memory means for transferring and receiving data to and from said digital processing means,
a fixed instruction generating means for generating operating code for said digital processing means and addresses for said memory means,
a read only memory for performing a squaring operation and having a l-bit address input and a k-bit output, the address input of which is bit position m to m+l−1 of the n-bit input data bus line of said digital processing means, and the output data of which is bit position n−k to n−1 of the n-bit output data bus line of said digital processing means,
an overflow detecting means having an input of bit positions m+l−1 to n−1 of sand n-bit input data bus line, and
a j-bit output digital saturation circuit means connected to bit positions n−j to n−1 of said n-bit output data bus line, where j, k, l, m and n are integers having a relationship expressed by:

j, k, l, m < n.

2. A digital signal processing apparatus as claimed in claim 1, wherein said digital processing means comprises an arithmetic logic unit and shifter circuit.

3. A digital signal processing apparatus as claimed in claim 1, wherein said memory means has a plurality of memories in each of which is stored input data for said squaring operation.

4. A digital signal processing apparatus as claimed in claim 1, further comprising a counter for counting operation passes, a clock input supplied to said counter in synchronism with one operation process cycle, address adding means for adding l-bit address data to data on bit position m to m+l−1 of an address bus line connected between said fixed instruction generating means and said memory means, and means for establishing an l-bit output of said counter as the address adding data when said fixed instruction generating means access an input data buffer region of said memory means.

5. A digital signal processing apparatus as recited in claim 1 wherein the integers k and l further satisfy a relationship expressed by:

k<2l.

6. A digital signal processing apparatus as recited in claim 1 wherein said overflow detecting means provides an output signal, said output signal provided as an input to said digital saturation circuit means, and wherein said digital saturation circuit means provides output signals to said n-bit output data bus line.

* * * * *